(12) United States Patent
Mallet et al.

(10) Patent No.: US 8,197,692 B2
(45) Date of Patent: Jun. 12, 2012

(54) POROUS MATERIALS FOR SOLID PHASE EXTRACTION AND CHROMATOGRAPHY AND PROCESSES FOR PREPARATION AND USE THEREOF

(75) Inventors: Claude R. Mallet, Attleboro, MA (US); John E. O'Gara, Ashland, MA (US); Darryl W. Brousmiche, Grafton, MA (US)

(73) Assignee: Waters Technologies Corporation, Milford, MA (US)

( * ) Notice: Subject to any disclaimer, the term of this patent is extended or adjusted under 35 U.S.C. 154(b) by 54 days.

(21) Appl. No.: 12/790,795

(22) Filed: May 28, 2010

(65) Prior Publication Data

US 2010/0300972 A1    Dec. 2, 2010

Related U.S. Application Data

(63) Continuation of application No. 10/782,397, filed on Feb. 18, 2004, now Pat. No. 7,731,844, which is a continuation-in-part of application No. 10/169,546, filed as application No. PCT/US99/13241 on Jun. 10, 1999, now Pat. No. 7,232,520.

(60) Provisional application No. 60/089,153, filed on Jun. 12, 1998.

(51) Int. Cl.
    *B01D 15/08* (2006.01)
(52) U.S. Cl. ............... 210/635; 210/656; 210/198.2; 210/502.1
(58) Field of Classification Search ............... 210/634, 210/635, 656, 659, 198.2; 96/101; 502/402; 521/32, 33; 525/326.9, 330.3, 330.4, 330.5
See application file for complete search history.

(56) References Cited

U.S. PATENT DOCUMENTS

| | | | |
|---|---|---|---|
| 2,540,985 A | 2/1951 | Jackson |
| 2,788,331 A | 4/1957 | Greer et al. |
| 2,801,224 A | 7/1957 | Greer |
| 2,824,844 A | 2/1958 | Gilwood |
| 3,499,960 A | 3/1970 | Stauffer et al. |
| 3,816,355 A | 6/1974 | Clemens |
| 3,946,749 A | 3/1976 | Papantoniou |
| 3,954,682 A | 5/1976 | Fein et al. |
| 3,985,540 A | 10/1976 | Fein et al. |
| 3,991,018 A | 11/1976 | Strop et al. |
| 4,000,098 A | 12/1976 | Hofstee |
| 4,101,461 A | 7/1978 | Strop et al. |

(Continued)

FOREIGN PATENT DOCUMENTS

EP    0852334    7/1998

(Continued)

OTHER PUBLICATIONS

Lieto, J. et al. "Polymer supports for catalysts," *Chemtech.* 46-53 (1983).

(Continued)

*Primary Examiner* — Ernest G Therkorn
(74) *Attorney, Agent, or Firm* — Edwards Wildman Palmer LLP; Peter C. Lauro, Esq.; Mark D. Russett

(57) ABSTRACT

Embodiments of the present invention are directed to porous materials for use in solid phase extractions and chromatography. The materials feature at least one hydrophobic component, at least one hydrophilic component and at least one ion-exchange functional group. The materials exhibit superior wetting and ion-exchange performance.

2 Claims, 2 Drawing Sheets

U.S. PATENT DOCUMENTS

| | | | |
|---|---|---|---|
| 4,192,921 A | 3/1980 | Dales | |
| 4,297,220 A | 10/1981 | Meitzner et al. | |
| 4,303,531 A | 12/1981 | Kawabata et al. | |
| 4,468,330 A | 8/1984 | Kamiyama et al. | |
| 4,523,959 A | 6/1985 | Exertier | |
| 4,622,288 A | 11/1986 | Yokoyama et al. | |
| 4,711,863 A | 12/1987 | Streat et al. | |
| 4,758,413 A | 7/1988 | Harris et al. | |
| 4,789,479 A | 12/1988 | Onitsuka et al. | |
| 4,828,710 A | 5/1989 | Itoh et al. | |
| 4,889,632 A | 12/1989 | Svec et al. | |
| 4,923,610 A | 5/1990 | Svec et al. | |
| 4,933,372 A | 6/1990 | Feibush et al. | |
| 4,952,349 A | 8/1990 | Svec et al. | |
| 4,954,262 A | 9/1990 | Aoki et al. | |
| 5,030,352 A | 7/1991 | Varady et al. | |
| 5,230,806 A | 7/1993 | Fritz et al. | |
| 5,238,992 A | 8/1993 | Outubuddin | |
| 5,278,339 A | 1/1994 | Cook | |
| 5,292,818 A | 3/1994 | Oishi et al. | |
| 5,292,828 A | 3/1994 | Jenkins et al. | |
| 5,431,807 A | 7/1995 | Frechet et al. | |
| 5,453,185 A | 9/1995 | Frechet et al. | |
| 5,587,323 A | 12/1996 | Lewis et al. | |
| 5,618,438 A | 4/1997 | Fritz et al. | |
| 5,728,457 A | 3/1998 | Frechet et al. | |
| 5,840,911 A | 11/1998 | Frei et al. | |
| 5,882,521 A | 3/1999 | Bouvier et al. | |
| 5,976,367 A | 11/1999 | Bouvier et al. | |
| 6,045,697 A | 4/2000 | Girot et al. | |
| 6,106,721 A | 8/2000 | Bouvier et al. | |
| 6,117,996 A | 9/2000 | Lowe et al. | |
| 6,238,565 B1 | 5/2001 | Hatch | |
| 6,248,798 B1 | 6/2001 | Slingsby et al. | |
| 6,322,695 B1 | 11/2001 | Lee et al. | |
| 6,362,245 B1 | 3/2002 | Takahashi et al. | |
| 6,686,035 B2 | 2/2004 | Jiang et al. | |
| 6,946,070 B2 | 9/2005 | Hammen et al. | |
| 7,232,520 B1 | 6/2007 | Lee et al. | |
| 7,442,299 B2 | 10/2008 | Lee et al. | |
| 7,731,844 B2 * | 6/2010 | Mallet et al. | 210/198.2 |
| 8,048,305 B2 * | 11/2011 | Lu et al. | 210/635 |
| 2002/0004561 A1 | 1/2002 | Takahashi et al. | |
| 2002/0043499 A1 | 4/2002 | Hammen et al. | |
| 2007/0205156 A1 | 9/2007 | Lee et al. | |
| 2009/0139323 A1 | 6/2009 | Lee et al. | |

FOREIGN PATENT DOCUMENTS

| | | |
|---|---|---|
| EP | 0982326 | 3/2000 |
| EP | 1159995 A2 | 12/2001 |
| JP | 2002-187904 A | 7/2002 |
| WO | WO 95/30467 | 11/1995 |
| WO | WO 99/64480 | 12/1999 |
| WO | WO 00/73782 | 12/2000 |

OTHER PUBLICATIONS

Mitchell, A. R. et al. "Preparation of aminomethyl-polystyrene resin by direct amidomethylation," *Tetrahedron Letters*. 42: 3795-8 (1976).

Unger, K. "Packings and stationary phases in chromatographic techniques," *Chromatographic Science Series*. 47: 585-720 (1990).

Mills, M. S. et al. "Application of mixed-mode, solid-phase extraction in environmental and clinical chemistry," *Journal of Chromatography*. 629: 11-21 (1993).

http://en.wikipedia.org/wilki/Amide Nov. 15, 2007.

Office Action mailed Aug. 3, 2011, in co-pending U.S. Appl. No. 12/855,300.

\* cited by examiner

POROUS MATERIALS FOR SOLID PHASE EXTRACTION AND CHROMATOGRAPHY AND PROCESSES FOR PREPARATION AND USE THEREOF

REFERENCE TO RELATED APPLICATIONS

The present application is a continuation of U.S. patent application Ser. No. 10/782,397, filed Feb. 18, 2004, now U.S. Pat. No. 7,731,844, which is a continuation-in-part of U.S. application Ser. No. 10/169,546 now U.S. Pat. No. 7,232,520, which entered the U.S. national stage on Jan. 16, 2003, as the U.S. national phase application of PCT international application No. PCT/US99/13241, filed on Jun. 10, 1999, which claims the benefit of U.S. provisional application Ser. No. 60/089,153, filed on Jun. 12, 1998. The present application also contains subject matter that is related to that disclosed and claimed in U.S. application Ser. No. 09/505,456, filed on Feb. 11, 2000, now U.S. Pat. No. 6,322,695, which is a continuation-in-part of PCT international application No. PCT/US99/13241, filed on Jun. 10, 1999, which claims priority to U.S. provisional application Ser. No. 60/089,153, filed on Jun. 12, 1998. The disclosures of all the aforementioned patent applications and the aforementioned patent are incorporated herein in their entireties by this reference.

BACKGROUND OF THE INVENTION

Solid phase extraction (SPE) is a chromatographic technique that is widely used, e.g., for preconcentration and cleanup of analytical samples, for purification of various chemicals, and for removal of toxic or valuable substances from aqueous solutions. SPE is usually performed using a column or cartridge containing an appropriate material or sorbent. SPE procedures have been developed using sorbents that can interact with analytes by hydrophobic, ion-exchange, chelation, sorption, and other mechanisms, to bind and remove the analytes from fluids.

Because different SPE applications can require different sorbents, there is a need for sorbents with novel properties that have unique selectivities. These include superior wetting characteristics, selective capture of analytes of interest, and non-retention of interfering analytes. Sorbents comprising porous particles having the aforementioned properties are described in WO 99/64480 and in U.S. Pat. No. 6,322,695B1.

However, a problem associated with porous particles is the passage or leaching of particles through the retaining frit of the separation device into the sample of interest. In addition to contamination of the sample, the passed particles can further negatively impact test methods and the HPLC systems that are used to test the samples. For example, the particles may clog or block in line filters or column frits which in turn lead to high system backpressures and ultimately HPLC pump shutdown.

Monolith materials have been developed in an attempt to overcome the problem of particle passage or leaching through frits. These include polymeric monoliths such as polymethacrylate monoliths (U.S. Pat. No. 5,453,185, U.S. Pat. No. 5,728,457); polystyrene—DVB monoliths (U.S. Pat. No. 4,889,632, U.S. Pat. No. 4,923,610, U.S. Pat. No. 4,952,349); charge incorporated polymethacrylate monoliths for the application of reversed-phase ion-pairing chromatography (U.S. Pat. No. 6,238,565); monoliths based on ROMP metathesis (WO 00073782); and (EP 852334) continuous monolith columns made from water-soluble polymerizable monomers, such as vinyl, allyl, acrylic and methacrylic compounds, without porogens but in the presence of high concentration of inorganic salts such as ammonium sulfate.

Polymeric monoliths are chemically stable against strongly alkaline and strongly acidic mobile phases, allowing flexibility in the choice of mobile phase pH. However, the prior art monoliths do not necessarily provide the unique selectivities and advantages that are needed for a variety of chromatographic applications, in particular SPE applications.

SUMMARY OF THE INVENTION

The invention is directed to novel porous materials that are useful in chromatographic processes, e.g., solid phase extraction, and that provide a number of advantages. Such advantages include superior wetting characteristics, selective capture of analytes of interest, and non-retention of interfering analytes. The invention also provides novel porous materials that overcome the problems of particle passage through frits.

Thus, in a first aspect, the invention provides a porous material comprising a copolymer of at least one hydrophobic monomer and at least one hydrophilic monomer, wherein said copolymer further comprises at least one ion-exchange functional moiety selected from the group consisting of an acyclic secondary amine exclusive of polyethylenimine, a cyclic tertiary amine, a substituted acyclic amine, and a substituted cyclic amine.

In a second aspect, the invention provides a copolymer having the formula I:

$$-(\text{-}A\text{-})_n\text{-}(\text{---}B\text{---})_m\text{-}(\text{---}C\text{---})_p\text{---} \tag{I}$$

and salts thereof, wherein the order of repeat units A, B and C may be random, block, or a combination of random and block;

wherein $$\frac{1}{100} < \frac{(p+n)}{m} < \frac{100}{1}$$

and $$\frac{1}{500} < \frac{p}{n} < \frac{100}{1}$$

wherein A is selected from the group consisting of

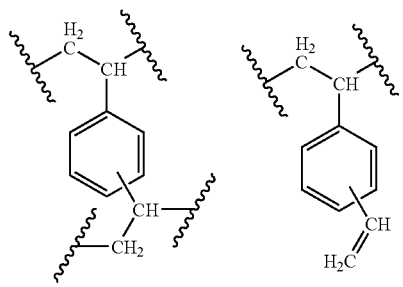

-continued

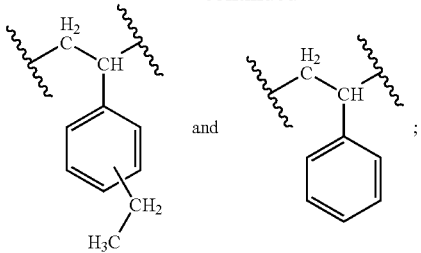

wherein B is selected from the group consisting of

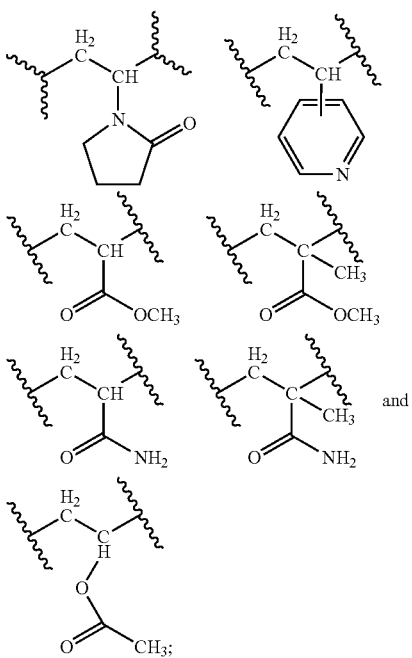

wherein C is modified A, wherein modified A is selected from the group consisting of

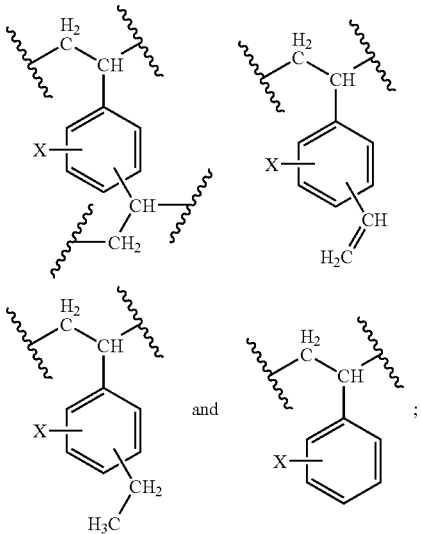

and
wherein X is —CR$_1$R$_2$NR$_3$R$_4$ wherein:
R$_1$ and R$_2$ are the same or different and each is hydrogen or C$_1$-C$_6$ alkyl;
R$_3$ and R$_4$ are the same or different and each is hydrogen, an electron withdrawing group, C$_1$-C$_{20}$ alkyl, C$_1$-C$_{20}$ alkyl substituted by an electron withdrawing group, or R$_3$ and R$_4$ taken together form a carbocyclic ring or a heterocyclic ring, wherein the carbocyclic ring or heterocyclic ring can be substituted by an electron withdrawing group, provided that (i) R$_1$, R$_2$, R$_3$, and R$_4$ are not all hydrogen; (ii) if R$_1$ and R$_2$ are hydrogen, then R$_3$ and R$_4$ are not both unsubstituted C$_1$-C$_{20}$ alkyl; and (iii) if R$_1$ and R$_2$ are hydrogen, and either of R$_3$ and R$_4$ is hydrogen, then the other of R$_3$ and R$_4$ is not polyethylenimine.

In accordance with the invention, the porous materials disclosed herein can take the form of porous particles or monoliths. Thus, in yet another aspect, the invention provides a porous material comprising a porous particle that comprises a copolymer described above with regard to the first and second aspects of the invention. Likewise, the invention provides a porous material comprising a porous monolith that comprises a copolymer described above with regard to the first and second aspects of the invention.

In another aspect, the invention also provides solid phase extraction and chromatography materials comprising porous materials of the invention.

In yet another aspect, the invention provides a separation device comprising a porous material of the invention. In a related aspect, the invention provides a solid phase extraction cartridge comprising a porous materials according to the invention.

The invention also provides a method for removing or isolating a component from a mixture. The method comprises contacting the mixture with a chromatographic material comprising the porous material according to the invention, to thereby remove or isolate the component from the mixture.

In another aspect, the invention provides a method for determining the level of a component in a mixture. The method comprises contacting the mixture with a chromatographic material comprising a porous material according to the invention under conditions that allow for sorption of the component onto the porous material; washing the chromatographic material having the sorbed component with a solvent under conditions so as to desorb the component from the porous materials; and determining the level of the desorbed component.

DETAILED DESCRIPTION OF THE INVENTION

Definitions

Figure 1:
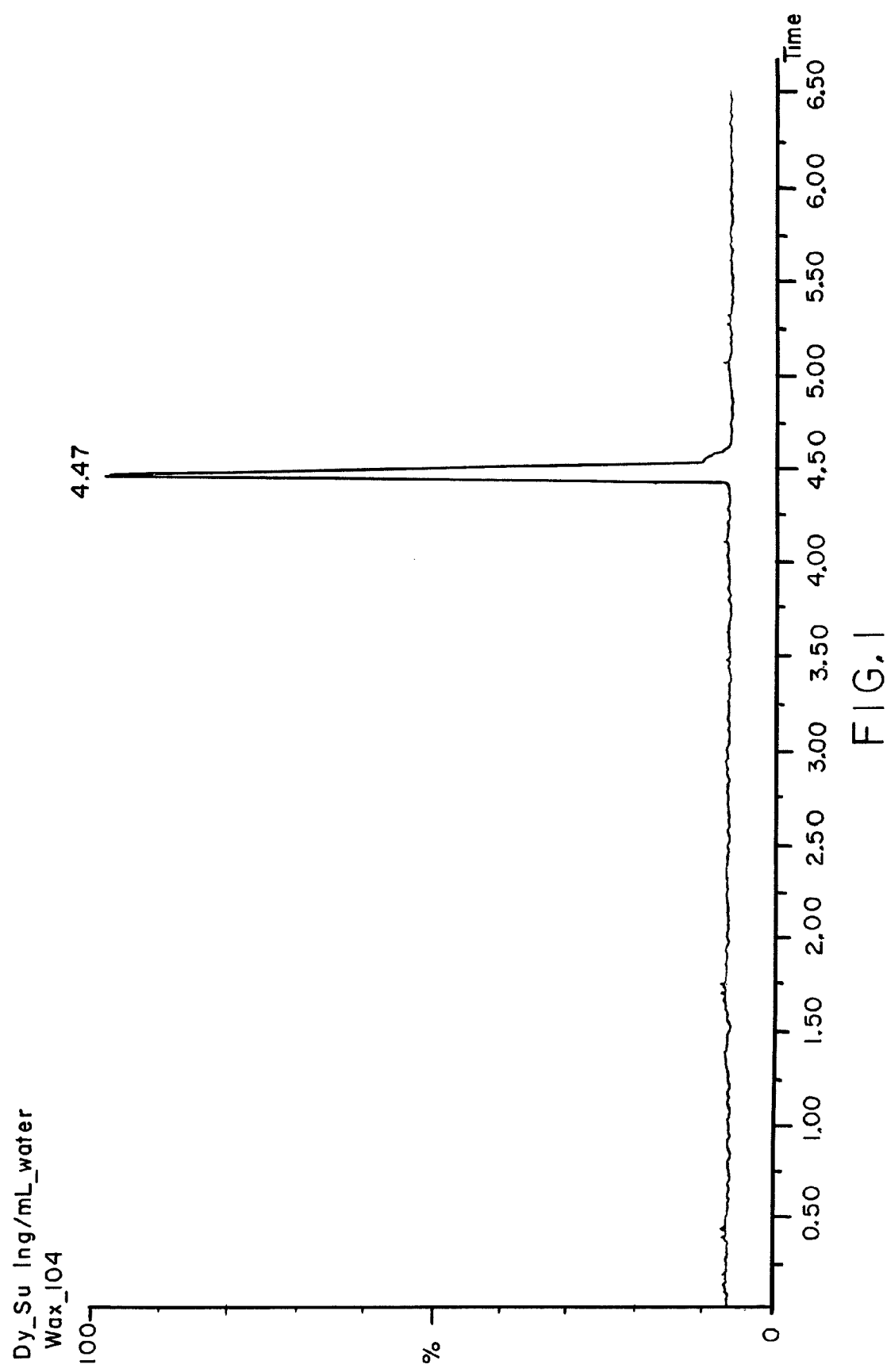
FIG. 1 depicts the total ion chromatogram (TIC) obtained using the product of Example 3b.

The present invention will be more fully illustrated by reference to the definitions set forth below.

The term "alicyclic group" includes closed ring structures of three or more carbon atoms. Alicyclic groups include cycloparaffins or naphthenes that are saturated cyclic hydrocarbons, cycloolefins that are unsaturated with two or more double bonds, and cycloacetylenes, which have a triple bond. They do not include aromatic groups. Examples of cycloparaffins include cyclopropane, cyclohexane, and cyclopentane.

Examples of cycloolefins include cyclopentadiene and cyclooctatetraene. Alicyclic groups also include fused ring structures and substituted alicyclic groups such as alkyl substituted alicyclic groups. In the instance of the alicyclics such substituents may further comprise a lower alkyl, a lower alkenyl, a lower alkoxy, a lower alkylthio, a lower alkylamino, a lower alkylcarboxyl, a nitro, a hydroxyl, —CF$_3$, —CN, or the like.

The term "aliphatic group" includes organic compounds characterized by straight or branched chains, typically having between 1 and 22 carbon atoms. Aliphatic groups include alkyl groups, alkenyl groups and alkynyl groups. In complex structures, the chains may be branched or cross-linked. Alkyl groups include saturated hydrocarbons having one or more carbon atoms, including straight-chain alkyl groups and branched-chain alkyl groups. Such hydrocarbon moieties may be substituted on one or more carbons with, for example, a halogen, a hydroxyl, a thiol, an amino, an alkoxy, an alkylcarboxy, an alkylthio, or a nitro group. Unless the number of carbons is otherwise specified, "lower aliphatic" as used herein means an aliphatic group, as defined above (e.g., lower alkyl, lower alkenyl, lower alkynyl), but having from one to six carbon atoms. Representative of such lower aliphatic groups, e.g., lower alkyl groups, are methyl, ethyl, n-propyl, isopropyl, 2-chloropropyl, n-butyl, sec-butyl, 2-aminobutyl, isobutyl, tert-butyl, 3-thiopentyl, and the like. As used herein, the term "nitro" means —NO$_2$; the term "halogen" designates —F, —Cl, —Br or —I; the term "thiol" means SH; and the term "hydroxyl" means —OH.

The terms "alkenyl" and "alkynyl" refer to unsaturated aliphatic groups analogous to alkyls, but which contain at least one double or triple bond respectively. Suitable alkenyl and alkynyl groups include groups having 2 to about 12 carbon atoms, preferably from 1 to about 6 carbon atoms.

The term "alkoxy" as used herein means an alkyl group, as defined above, having an oxygen atom attached thereto. Representative alkoxy groups include groups having 1 to about 12 carbon atoms, preferably 1 to about 6 carbon atoms, e.g., methoxy, ethoxy, propoxy, tert-butoxy and the like.

The term "alkyl" includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has 30 or fewer carbon atoms in its backbone, e.g., C$_1$-C$_{30}$ for straight chain or C$_3$-C$_{30}$ for branched chain. In certain embodiments, a straight chain or branched chain alkyl has 20 or fewer carbon atoms in its backbone, e.g., C$_1$-C$_{20}$ for straight chain or C$_3$-C$_{20}$ for branched chain, and more preferably 18 or fewer. Likewise, preferred cycloalkyls have from 4-10 carbon atoms in their ring structure, and more preferably have 4-7 carbon atoms in the ring structure. The term "lower alkyl" refers to alkyl groups having from 1 to 6 carbons in the chain, and to cycloalkyls having from 3 to 6 carbons in the ring structure.

Moreover, the term "alkyl" (including "lower alkyl") as used throughout the specification and claims includes both "unsubstituted alkyls" and "substituted alkyls," the latter of which refers to alkyl moieties having substituents replacing a hydrogen on one or more carbons of the hydrocarbon backbone. Such substituents may include, for example, halogen, hydroxyl, alkylcarbonyloxy, arylcarbonyloxy, alkoxycarbonyloxy, aryloxycarbonyloxy, alkylcarbonyl, alkoxycarbonyl, aminocarbonyl, alkylthiocarbonyl, alkoxyl, cyano, alkyl amino, arylamino, diarylamino, and alkylarylamino, acylamino (including alkylcarbonylamino, arylcarbonylamino, carbamoyl and ureido), amidino, imino, sulfhydryl, alkylthio, arylthio, thiocarboxylate, sulfamoyl, sulfonamido, nitro, trifluoromethyl, cyano, azido, heterocycyl, aralkyl, or an aromatic or heteroaromatic moiety. It will be understood by those skilled in the art that the moieties substituted on the hydrocarbon chain may themselves be substituted, if appropriate.

Cycloalkyls may be further substituted, e.g., with the substituents described above. An "aralkyl" moiety is an alkyl substituted with an aryl, e.g., having 1 to 3 separate or fused rings and from 6 to about 18 carbon ring atoms, e.g., phenylmethyl (benzyl).

The term "alkylamino" as used herein means an alkyl group, as defined above, having an amino group attached thereto. Suitable alkylamino groups include groups having 1 to about 12 carbon atoms, preferably from 1 to about 6 carbon atoms. The term "amino," as used herein, refers to an unsubstituted or substituted moiety of the formula —NR$_a$R$_b$, in which R$_a$ and R$_b$ are each independently hydrogen, alkyl, aryl, or heterocyclyl, but R$_a$ and R$_b$ are both not alkyl, or R$_a$ and R$_b$, taken together with the nitrogen atom to which they are attached, form a cyclic moiety having from 3 to 8 atoms in the ring. An "amino-substituted amino group" refers to an amino group in which at least one of R$_a$ and R$_b$, is further substituted with an amino group.

Thus, the terms "alkylamino" and "amino" include acyclic primary amines such methylamine, ethylamine, propylamine, isopropylamine, butylamine, sec-butylamine, iso-butylamine, tert-butylamine, pentylamine, 1,1-dimethylpropylamine, 1,2-dimethylpropylamine, 1-ethylpropylamine, 2-methylbutylamine, isopentylamine, hexylamine, 1,3-dimethylbutylamine, 3,3-dimethylamine, heptylamine, 2-aminoheptane, octylamine, 1,5-dimethylhexylamine, 2-ethylhexylamine, 1-methylheptylamine, tert-octylamine, nonylamine, decylamine, undecylamine, dodecylamine, tridecylamine, tetradecylamine, pentadecylamine, hexadecylamine, heptadecylamine, octadecylamine, nonadecylamine, and eicosylamine. Preferred primary amines include propylamine, isopropylamine, butylamine, sec-butylamine, iso-butylamine, pentylamine, isopentylamine, hexylamine, heptylamine, 2-aminoheptane, octylamine, 2-ethylhexylamine, dodecylamine, or octadecylamine.

The terms "alkylamino" and "amino" also include cyclic secondary amines such as azirane, azetane, azolane, azinane, azepane, azocane, azonane, azecane, diazatene, diazolane, diazinane, N-methyldiazinane, diazepane, diazocane, diazonane, diazecane, and imidazole. Preferred cyclic secondary amines include azinane, diazinane and N-methyl-diazinane.

The term "alkylthio" refers to an alkyl group, as defined above, having a sulfhydryl group attached thereto. Suitable alkylthio groups include groups having 1 to about 12 carbon atoms, preferably from 1 to about 6 carbon atoms. The term "alkylcarboxyl" as used herein means an alkyl group, as defined above, having a carboxyl group attached thereto.

The term "aromatic group" includes unsaturated cyclic hydrocarbons containing one or more rings. Aromatic groups include 5- and 6-membered single-ring groups which may include from zero to four heteroatoms, for example, benzene, pyrrole, furan, thiophene, imidazole, oxazole, thiazole, triazole, pyrazole, pyridine, pyrazine, pyridazine and pyrimidine, and the like. The aromatic ring may be substituted at one or more ring positions with, for example, a halogen, a lower alkyl, a lower alkenyl, a lower alkoxy, a lower alkylthio, a lower alkylamino, a lower alkylcarboxyl, a nitro, a hydroxyl, —CF$_3$, —CN, or the like.

The term "aryl" includes 5- and 6-membered single-ring aromatic groups that may include from zero to four heteroatoms, for example, unsubstituted or substituted benzene, pyrrole, furan, thiophene, imidazole, oxazole, thiazole, triazole, pyrazole, pyridine, pyrazine, pyridazine and pyrimidine, and the like. Aryl groups also include polycyclic fused aromatic groups such as naphthyl, quinolyl, indolyl, and the like. The aromatic ring may be substituted at one or more ring positions with such substituents, e.g., as described above for alkyl groups. Suitable aryl groups include unsubstituted and substituted phenyl groups. The term "aryloxy" as used herein means an aryl group, as defined above, having an oxygen atom attached thereto. The term "aralkoxy" as used herein means an aralkyl group, as defined above, having an oxygen atom attached thereto. Suitable aralkoxy groups have 1 to 3 separate or fused rings and from 6 to about 18 carbon ring atoms, e.g., O-benzyl.

The term "block ordering" is intended to include ordering in which individual units are joined in a pattern or repeated sequence.

The term "conjugate acid of an amine" describes a protonated amine that is positively charged.

The term "copolymer" is intended to include a polymer comprising two or more different monomers.

The term "electron withdrawing group" describes a substituent or group that has the effect of lowering the average $pK_a$ of the conjugate acid of an amine substituted with the electron withdrawing group as compared to the conjugate acid of that amine without the electron withdrawing group. Electron withdrawing groups in accordance with the invention include halogens, aromatic groups, unsaturated groups, ethers, thioethers, nitriles, nitro groups, esters, amides, carbamates, ureas, carbonates, sulfonamides, sulfones, and sulfoxides. In addition, the term is intended to include heteroatoms that substitute for ring carbon atoms in a heterocycle. Preferred electron withdrawing groups include halogens, ethers, or an aromatic group.

The term "haloalkyl" is intended to include alkyl groups as defined above that are mono-, di- or polysubstituted by halogen, e.g., chloromethyl, fluoromethyl, bromomethyl, iodomethyl, and trifluoromethyl.

The term "heteroatom" as used herein means an atom of any element other than carbon or hydrogen. Preferred heteroatoms are nitrogen, oxygen, sulfur and phosphorus.

The term "heterocyclic group" includes closed ring structures in which one or more of the atoms in the ring is an element other than carbon, for example, nitrogen, sulfur, or oxygen. Heterocyclic groups may be saturated or unsaturated and heterocyclic groups such as pyrrole and furan may have aromatic character. They include fused ring structures such as quinoline and isoquinoline. Other examples of heterocyclic groups include pyridine and purine. Heterocyclic groups may also be substituted at one or more constituent atoms with, for example, a halogen, a lower alkyl, a lower alkenyl, a lower alkoxy, a lower alkylthio, a lower alkylamino, a lower alkylcarboxyl, a nitro, a hydroxyl, —$CF_3$, —CN, or the like. Suitable heteroaromatic and heteroalicyclic groups generally will have 1 to 3 separate or fused rings with 3 to about 8 members per ring and one or more N, O or S atoms, e.g., coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholino and pyrrolidinyl.

Thus, the term "heterocyclic group" includes moieties such as azirane, azetane, azolane, azinane, azepane, azocane, azonane, and azecane that are heterocyclic molecules containing a single nitrogen within a 3-, 4-, 5-, 6-, 7-, 8-, 9-, and 10-membered ring respectively. These molecules may also have additional fused rings of the same or a different structure and may also have unsaturation. These molecules may be further substituted with a variety groups including aliphatic groups, alicyclic groups, heterocyclic groups, aromatic groups, and the like.

The term "heterocyclic group" also includes moieties such as diazatene, diazolane, diazinane, diazepane, diazocane, diazonane, and diazecane that are heterocyclic molecules containing two nitrogens within a 4-, 5-, 6-, 7-, 8-, 9- and 10-membered ring respectively. These molecules may also have additional fused rings of the same or a different structure and may also have unsaturation. These molecules may be further substituted with a variety groups including aliphatic groups, alicyclic groups, heterocyclic groups, aromatic groups, and the like. N-methylpiperazine is an example of a substituted diazinane. Imidazole is an example of an unsaturated diazolane.

The term "heterocyclic group" further includes moieties such as oxazetane, oxazolane, oxazinane, oxazepane, oxazocane, oxazonane, and oxazecane" that are heterocyclic molecules containing one oxygen and one nitrogen within a 4-, 5-, 6-, 7-, 8-, 9-, and 10-membered ring respectively. These molecules may also have additional fused rings of the same or a different structure and may also have unsaturation. These molecules may be further substituted with a variety groups including aliphatic groups, alicyclic groups, heterocyclic groups, aromatic groups, and the like. Morpholine is an example of an oxazinane.

The term "heterocyclic group" also includes moieties such as thiazetane, thiazolane, thiazinane, thiazepane, thiazocane, thiazonane, and thiazecane that are heterocyclic molecules containing one sulfur and one nitrogen within a 4-, 5-6-, 7-, 8-, 9, and 10-membered ring respectively. These molecules may also have additional fused rings of the same or a different structure and may also have unsaturation. These molecules may be further substituted with a variety groups including aliphatic groups, alicyclic groups, heterocyclic groups, aromatic groups, and the like.

The term "hydrophilic" describes having an affinity for, attracting, adsorbing or absorbing water.

The term "hydrophobic" describes lacking an affinity for, repelling, or failing to adsorb or absorb water.

The term "ion-exchange functional group" is intended to include a group where the counter-ion is partially free and can readily be exchanged for other ions of the same sign.

The term "mole percent" describes the mole fraction, expressed as a percent, of the monomer of interest relative to the total moles of the various (two or more) monomers which compose the copolymer of the porous material of the invention.

The term "monolith" is intended to include a porous, three-dimensional material having a continuous interconnected pore structure in a single piece. A monolith is prepared, for example, by casting precursors into a mold of a desired shape. The term monolith is meant to be distinguished from a collection of individual particles packed into a bed formation, in which the end product still comprises individual particles in bed formation.

The term "monomer" is intended to include a molecule comprising one or more polymerizable functional groups prior to polymerization, or a repeating unit of a polymer.

The term "porous material" is intended to include a member of a class of porous crosslinked polymers penetrated by pores through which solutions can diffuse. Pores are regions between densely packed polymer chains.

The term "random ordering" is intended to include ordering in which individual units are joined randomly.

The term "solid phase extraction" is intended to include a process employing a solid phase for isolating classes of molecular species from fluid phases such as gases and liquids by, e.g., sorption, ion-exchange, chelation, size exclusion (molecular filtration), affinity or ion pairing mechanisms.

The term "sorption" describes the ability of a material to take up and hold another material by absorption or adsorption.

Compositions and Methods of the Invention

The invention provides a porous material comprising a copolymer of a least one hydrophobic monomer and at least one hydrophilic monomer, wherein said copolymer further comprises at least one ion-exchange functional moiety selected from the group consisting of an acyclic secondary amine exclusive of polyethylenimine, a cyclic tertiary amine, a substituted acyclic amine, and a substituted cyclic amine. Preferably, the porous material has a specific surface area in the range from about 50 to about 850 square meters per gram and pores having a diameter ranging from about 0.5 nm to about 100 nm. In certain embodiments, the porous material is incorporated in a matrix.

In certain embodiments, the porous materials of the invention take the form of porous particles, e.g., beads, pellets, or any other form desirable for use. The porous particles can have, e.g., a spherical shape, a regular shape or an irregular shape. Preferably, the particles are beads having a diameter in the range from about 3 to about 500 µm, preferably from about 20 to about 200 µm.

In other embodiments, the porous materials of the invention take the form of porous monoliths. In certain embodiments, the monoliths have the following characteristics: surface area ranging from about 50 to about 800 m$^2$/g, more particularly about 300 to about 700 m$^2$/g; pore volume ranging from about 0.2 to about 2.5 cm$^3$/g, more particularly about 0.4 to about 2.0 cm$^3$/g, still more particularly about 0.6 to about 1.4 cm$^3$/g; and pore diameter ranging from about 20 to about 500 Å, more particularly about 50 to 300 Å, still more particularly about 80 to about 150 Å.

The porous materials of the invention comprise a copolymer comprising a least one hydrophobic monomer and at least one hydrophilic monomer. In certain embodiments, the copolymer of the invention is non-sulfonated.

In certain embodiments the hydrophobic monomer comprises an aromatic carbocyclic group, e.g., a phenyl group or a phenylene group, or a straight chain $C_2$-$C_{18}$-alkyl group or a branched chain $C_2$-$C_{18}$-alkyl group. The hydrophobic monomer can be, e.g., styrene or divinylbenzene. A preferred copolymer is a poly(divinylbenzene-co-N-vinylpyrrolidone).

In certain embodiments, the hydrophilic monomer comprises a heterocyclic group, e.g., a saturated, unsaturated or aromatic heterocyclic group. Examples include nitrogen-containing heterocyclic groups, e.g., a pyridyl group, e.g., 2-vinylpyridine, 3-vinylpyridine or 4-vinylpyridine, or a pyrrolidonyl group, e.g., N-vinylpyrrolidone.

In one embodiment, the hydrophobic monomer is divinylbenzene or styrene, and the hydrophilic monomer is N-vinylpyrrolidone or N-vinyl acetamide. In a specific embodiment, the copolymer is a poly(divinylbenzene-co-N-vinylpyrrolidone). Preferably, the porous material comprises at least about 12 mole percent N-vinylpyrrolidone. More preferably, the porous material comprises at least about 30 mole percent N-vinylpyrrolidone.

The invention also provides porous materials wherein the hydrophobic monomer is substituted by at least one haloalkyl group, and the ion-exchange functional moiety is formed by reaction of the haloalkyl group with an appropriate starting amine to form an amine selected from the group consisting of an acyclic secondary amine, a cyclic tertiary amine, a substituted acyclic amine, and a substituted cyclic amine. In certain embodiments, the haolalkyl group is fluoromethyl, choromethyl, bromomethyl or iodomethyl. In one embodiment, the haloalkyl group is chloromethyl.

Examples of primary amines that can be used in accordance with the invention include methylamine, ethylamine, propylamine, isopropylamine, butylamine, sec-butylamine, iso-butylamine, tert-butylamine, pentylamine, 1,1-dimethylpropylamine, 1,2-dimethylpropylamine, 1-ethylpropylamine, 2-methylbutylamine, isopentylamine, hexylamine, 1,3-dimethylbutylamine, 3,3-dimethylamine, heptylamine, 2-aminoheptane, octylamine, 1,5-dimethylhexylamine, 2-ethylhexylamine, 1-methylheptylamine, tert-octylamine, nonylamine, decylamine, undecylamine, dodecylamine, tridecylamine, tetradecylamine, pentadecylamine, hexadecylamine, heptadecylamine, octadecylamine, nonadecylamine, and eicosylamine. In certain embodiments, the primary amine is propylamine, isopropylamine, butylamine, sec-butylamine, iso-butylamine, pentylamine, isopentylamine, hexylamine, heptylamine, 2-aminoheptane, octylamine, 2-ethylhexylamine, dodecylamine, or octadecylamine.

Examples of cyclic secondary amines in accordance with the invention include azirane, azetane, azolane, azinane, azepane, azocane, azonane, azecane, diazatene, diazolane, diazinane, diazepane, diazocane, diazonane, diazecane, imidazole, oxazetane, oxazolane, oxazinane, oxazepane, oxazocane, oxazonane, oxazecane, thiazetane, thiazolane, thiazinane, thiazepane, thiazocane, thiazonane, and thiazecane. In one embodiment, the cyclic secondary amine is 1,4-oxazinane. In another embodiment, the cyclic secondary amine is azinane. In yet another embodiment, the cyclic secondary amine is diazinane.

In accordance with the invention, the ion-exchange functional moiety can be formed from a substituted acyclic amine or a substituted cyclic amine. The substitution can be at any of the ring atoms, including heteroatoms. For example, in certain embodiments, the ion-exchange functional moiety is a substituted cyclic secondary amine, e.g., N-methyldiazinane and 4-methylpiperidine.

In other embodiments, the aforesaid amines are advantageously substituted by an electron withdrawing group. In certain embodiments, the electron withdrawing group is selected from the group consisting of halogens, aromatic groups, unsaturated groups, ethers, thioethers, nitriles, nitro groups, esters, amides, carbamates, ureas, carbonates, sulfonamides, sulfones, sulfoxides and heteroatoms, e.g., N, O and S. In certain embodiments, the electron withdrawing group is a halogen, an ether, or an aromatic group.

In accordance with the invention, the electron withdrawing group of the amine has the effect of lowering the average $pK_a$ of the conjugate acid of the amine as compared to the conjugate acid of the amine without the electron withdrawing group. In certain embodiments, the $pK_a$ ranges from about 5 to about 7.

In certain embodiments, the acyclic amine substituted with an electron withdrawing group includes benzylamine, N-methylbenzylamine, N-ethylbenzylamine, N-propylbenzylamine, N-butylbenzylamine, N-pentylbenzylamine, N-hexylbenzylamine, N-heptylbenzylamine, N-octylbenzylamine, N-nonylbenzylamine, N-decylbenzylamine, N-undecylbenzylamine, N-dodecylbenzylamine, N-tridecylbenzylamine, N-tetradecylbenzylamine, N-pentadecylbenzylamine, N-hexadecylbenzylamine, N-heptadecylbenzylamine, N-octadecylbenzylamine, dibenzylamine, aniline, N-methylaniline, N-ethylaniline, N-propylaniline, N-butylaniline, N-pentylaniline, N-hexylaniline, N-heptylaniline, N-octylaniline, N-nonylaniline, N-decylaniline, N-undecylaniline, N-dodecylaniline, N-tridecylaniline, N-tetradecylaniline, N-pentadecylaniline, N-hexadecylaniline, N-heptadecylaniline, N-octadecylaniline, bis(2,2,2-trifluoromethyl)amine, phenethylamine, N-methylphenethylamine, 4-methylphenethylamine, 3-phenylpropylamine, 1-methyl-3-phenylpropylamine, N-isopropylbenzylamine, and 4-phenylbutylamine. In certain preferred embodiments, the acyclic amine substituted with an electron withdrawing group is benzylamine, N-methylbenzylamine, or phenethylamine. In a preferred embodiment, the acyclic amine substituted with an electron withdrawing group is N-methylbenzylamine.

In other embodiments, cyclic secondary amines substituted with an electron withdrawing group include oxazetane, oxazolane, oxazinane, oxazepane, oxazocane, oxazonane, oxazecane, thiazetane, thiazolane, thiazinane, thiazepane, thiazocane, thiazonane, and thiazecane. In one embodiment, the cyclic secondary amine is 1,4-oxazinane. In these embodiments, one of ordinary skill in the art will appreciate that the electron withdrawing group is a second heteroatom that has substituted for a carbon atom in the ring. For example, the ring carbon adjacent to the nitrogen atom in azetidine is substituted by an oxygen to yield oxazetane, an amine encompassed by the term "cyclic secondary amine substituted with an electron withdrawing group".

The porous materials, in either porous particle or monolith form, are advantageously used for solid phase extraction or chromatography. In a one embodiment, the porous material comprises at least one porous particle, and more preferably a plurality of porous particles. In one embodiment, the porous material comprises the copolymer poly(divinylbenzene-co-N-vinylpyrrolidone). In a related embodiment, the poly(divinylbenzene-co-N-vinylpyrrolidone) has ion-exchange functional moieties present at a concentration of about 0.01 to about 1.0 milliequivalents per gram of porous material.

In another aspect, porous materials of the invention, in either porous particle or monolith form, comprise novel copolymers. These copolymers have the formula I:

         (I)

and salts thereof, wherein the order of repeat units A, B and C may be random, block, or a combination of random and block;

wherein $$\frac{1}{100} < \frac{(p+n)}{m} < \frac{100}{1}$$
and
$$\frac{1}{500} < \frac{p}{n} < \frac{100}{1}$$

wherein A is selected from the group consisting of

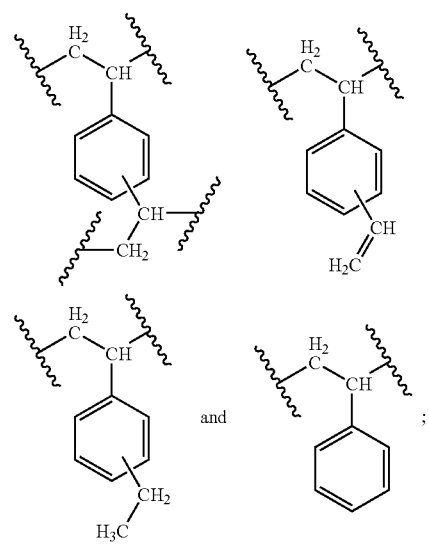

wherein B is selected from the group consisting of

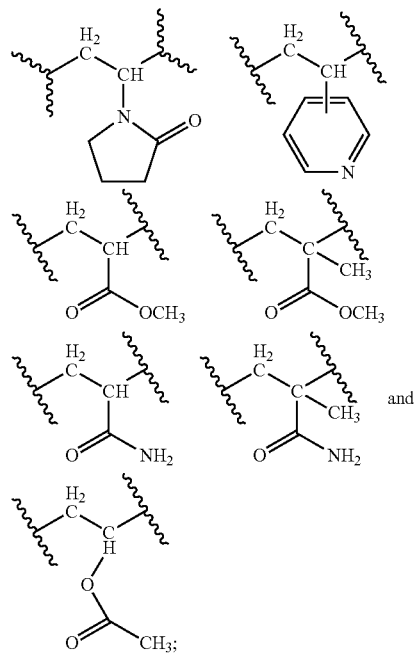

wherein C is modified A, wherein modified A is selected from the group consisting of

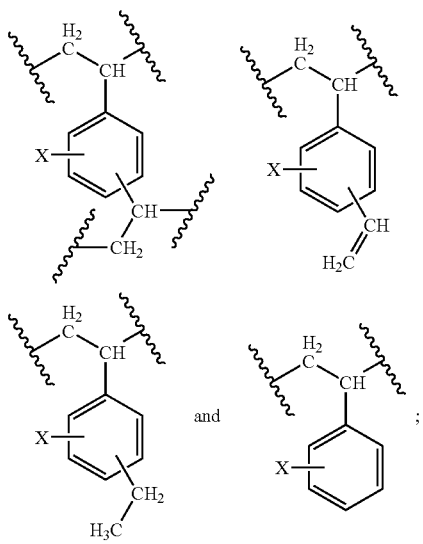

and wherein X is —CR₁R₂NR₃R₄ wherein:

R$_1$ and R$_2$ are the same or different and each is hydrogen or C$_1$-C$_6$ alkyl;

R$_3$ and R$_4$ are the same or different and each is hydrogen, an electron withdrawing group, C$_1$-C$_{20}$ alkyl, C$_1$-C$_{20}$ alkyl substituted by an electron withdrawing group, or R$_3$ and R$_4$ taken together form a carbocyclic ring or a heterocyclic ring, wherein the carbocyclic ring or heterocyclic ring can be substituted by an electron withdrawing group, provided that (i) R$_1$, R$_2$, R$_3$, and R$_4$ are not all hydrogen; (ii) if R$_1$ and R$_2$ are hydrogen, then R$_3$ and R$_4$ are not both unsubstituted C$_1$-C$_{20}$ alkyl; and (iii) if R$_1$ and R$_2$ are hydrogen, and either of R$_3$ and R$_4$ is hydrogen, then the other of R$_3$ and R$_4$ is not polyethylenimine.

In certain embodiments, the repeat unit of A is divinylbenzene or styrene. In certain embodiments, the repeat unit of B is N-vinylpyrrolidone or N-vinyl acetamide. In a preferred embodiment, the copolymer is a poly(divinylbenzene-co-N-vinylpyrrolidone) copolymer.

In one embodiment, A and B form a porous particle. In another embodiment, A and B form a porous monolith.

The ion-exchange functional group is represented by X in formula I above. Preferably, the ion-exchange functional groups are present at a concentration of about 0.01 to about 1.0, more preferably at a concentration of about 0.2 to about 0.8, more preferably yet at a concentration of about 0.4 to about 0.6, and still more preferably at a concentration of about 0.5 milliequivalents per gram of porous material.

In certain embodiments, the ion-exchange functional moiety represented by X is an amine selected from the group consisting of an acyclic secondary amine exclusive of polyethylenimine, a cyclic tertiary amine, a substituted acyclic amine, and a substituted cyclic amine. In such embodiments, the ion-exchange functional moiety is formed by reaction of a haloalkyl group with an appropriate starting amine to form the amine selected from the group consisting of an acyclic secondary amine, a cyclic tertiary amine, a substituted acyclic amine, and a substituted cyclic amine.

More particularly, the haloalkyl group, either introduced at the appropriate position on the phenyl ring after copolymerization (see Example 2 below) or as a pre-existing substituent on the phenyl ring of repeat unit C (see Example 4 below), is reacted with the appropriate starting amines (see Examples 3 and 5 below) in accordance with reactions and under conditions well-known to those of ordinary skill in the art. The appropriate starting amine can be any of the primary amines, cyclic secondary amines, substituted acyclic amines and substituted cyclic secondary amines described above.

In certain embodiments of the copolymer of formula I above, the electron withdrawing group is selected from the group consisting of halogens, aromatic groups, e.g., pyridyl, hydroxy groups, unsaturated groups, ethers, thioethers, nitriles, nitro groups, esters, amides, carbamates, ureas, carbonates, sulfonamides, sulfones, and sulfoxides. In certain embodiments, the electron withdrawing group is a halogen, an ether, or an aromatic group.

In accordance with the invention, X can be any of the following moieties:

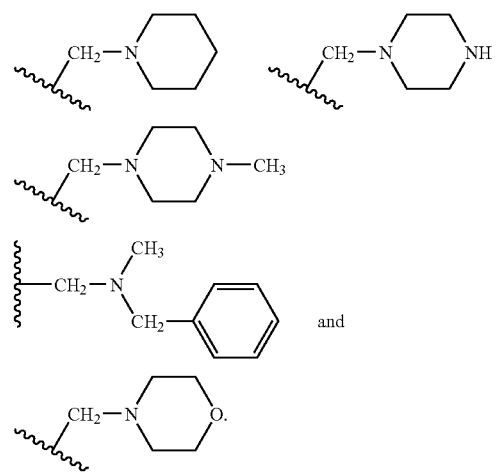

Preferred copolymers of Formula I include the following:

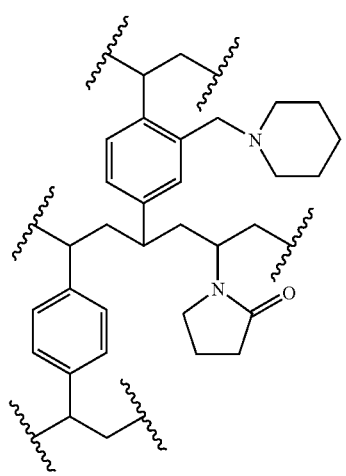

-continued

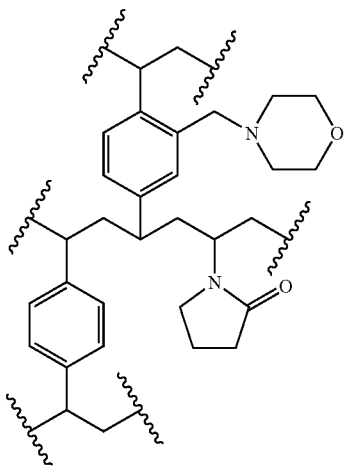

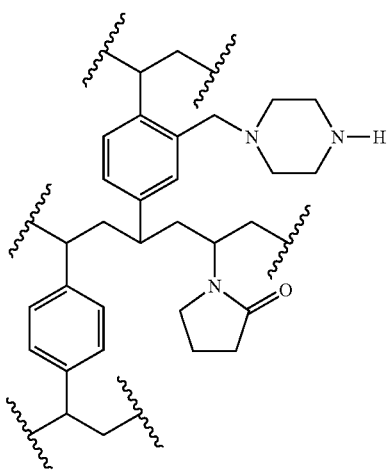

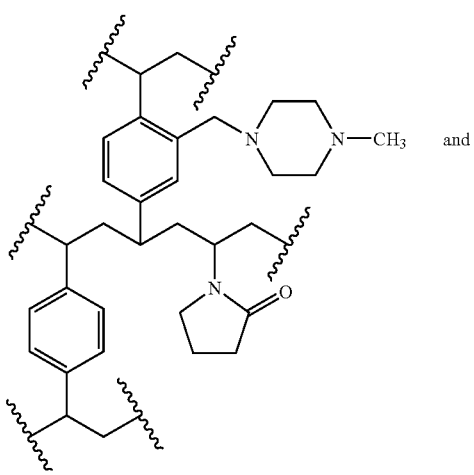

and

-continued

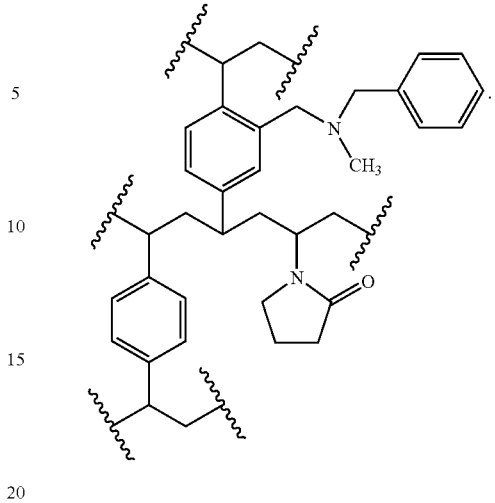

The porous materials of the invention can be prepared, e.g., by functionalizing, i.e., chemically altering, a copolymer having at least one hydrophobic repeat unit and at least one hydrophilic repeat unit. The order of repeat units may be random, block, or combinations of random and block.

The hydrophobic repeat unit may be derived from a variety of hydrophobic monomer reagents possessing one or more polymerizable moieties, capable of undergoing polymerization, e.g., a free radical-mediated polymerization. Examples of hydrophobic monomers include but are not limited to divinylbenzene, styrene, ethylvinylbenzene, and vinylbenzylchloride. Preferably, the hydrophobic monomer is divinylbenzene.

The hydrophilic repeat unit may be derived from a variety of hydrophilic monomer reagents possessing one or more polymerizable moieties, capable of undergoing polymerization, e.g., a free radical-mediated polymerization. Examples of hydrophilic monomers include but are not limited to N-vinylpyrrolidone, N-vinylacetamide, N-vinylpyridine, methacrylate, methyl methacrylate, vinyl acetate, acrylamide or methacrylamide. Preferably, the hydrophilic monomer is N-vinylpyrrolidone.

The copolymer can be prepared via a number of processes and mechanisms including, but not limited to, chain addition and step condensation processes, radical, anionic, cationic, ring-opening, group transfer, metathesis, and photochemical mechanisms. The copolymer can be prepared via standard synthetic methods known to those skilled in the art, e.g., as described in Example 1. Such a copolymer, e.g., poly(divinylbenzene-co-N-vinylpyrrolidone), can be functionalized by the addition of an ion-exchange functional group, e.g., the X group defined above in formula I. In a preferred embodiment, X is

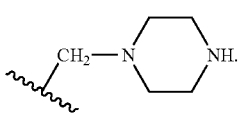

The novel materials of the invention, e.g., in the form of porous particles or monoliths, can be used for solid phase extraction and chromatography. Thus, the invention also provides a porous material for solid phase extraction or chromatography comprising at least one ion-exchange functional group, at least one hydrophilic component and at least one hydrophobic component. The ion-exchange functional groups enable the porous material to interact with basic and cationic solutes. The hydrophilic polar components enable the porous material to have polar interactions and hydrogen bonding capabilities with solutes. The hydrophobic components enable the porous material to have affinity towards nonpolar solutes through hydrophobic interaction. Since the porous materials of this invention have a combination of various interaction forces towards solutes, they are very useful materials for, e.g., solid phase extraction, ion-exchange, and liquid chromatography applications. For example, these novel porous materials can be used to bind, recover and/or remove solutes from fluids.

The invention also provides a method for removing or isolating a component, e.g., a solute, from a mixture. A solution having a solute is contacted with a porous material of the invention under conditions that allow for sorption of the solute to the porous material.

The solute can be, e.g., any molecule having a hydrophobic, hydrophilic, or ionic interaction or a combination of two or three of these interactions. Preferably, the solute is an organic compound of polarity suitable for adsorption onto the porous material. Such solutes include, e.g., drugs, pesticides, herbicides, toxins and environmental pollutants, e.g., resulting from the combustion of fossil fuels or other industrial activity, such as metal-organic compounds comprising a heavy metal such mercury, lead or cadmium. The solutes can also be metabolites or degradation products of the foregoing materials. Solutes also include, e.g., biomolecules, such as proteins, peptides, hormones, polynucleotides, vitamins, cofactors, metabolites, lipids and carbohydrates.

The solution e.g., can comprise water, an aqueous solution, or a mixture of water or an aqueous solution and a water-miscible polar organic solvent, e.g., methanol, ethanol, N,N-dimethylformamide, dimethylsulfoxide or acetonitrile. In a preferred embodiment, the solution is an acidic, basic or neutral aqueous, i.e., between about 1% and about 99% water by volume, solution. The solution comprising the solute can, optionally, further contain one or more additional solutes. In one embodiment, the solution is an aqueous solution which includes a complex variety of solutes. Solutions of this type include, e.g., blood, plasma, urine, cerebrospinal fluid, synovial fluid and other biological fluids, including, e.g., extracts of tissues, such as liver tissue, muscle tissue, brain tissue or heart tissue. Such extracts can be, e.g., aqueous extracts or organic extracts which have been dried and subsequently reconstituted in water or in a water/organic mixture. Solutions also include, e.g., ground water, surface water, drinking water or an aqueous or organic extract of an environmental sample, such as a soil sample. Other examples of solutions include a food substance, such as a fruit or vegetable juice or milk or an aqueous or aqueous/organic extract of a food substance, such as fruit, vegetable, cereal or meat. Other solutions include, e.g., natural products extractions from plants and broths.

The solution can be contacted with the porous material in any fashion which allows sorption of the solute to the porous material, such as a batch or chromatographic process. For example, the solution can be forced through a porous polymer column, disk or plug, or the solution can be stirred with the porous material, such as in a batch-stirred reactor. The solution can also be added to a porous material-containing well of a microtiter plate. The porous material can take the form of a monolith or particle, e.g., beads or pellets. The solution is contacted with the porous material for a time period sufficient for the solute of interest to substantially sorb onto the porous material. This period is typically the time necessary for the solute to equilibrate between the porous material surface and the solution. The sorption or partition of the solute onto the porous material can be partial or complete.

The invention also includes a method for analytically determining the level of solute in a solution. A solution having a solute is contacted with a porous material under conditions so as to allow sorption of the solute to the porous material. The material comprises at least one ion-exchange functional group, at least one hydrophilic polar component and at least one hydrophobic component. The porous material having the sorbed solute is washed with a solvent under conditions so as to desorb the solute from the porous material. The level of the desorbed solute present in the solvent after the washing is analytically determined.

The solution contacted with the porous material can comprise the solute of interest in dilute form, e.g., at a concentration too low for accurate quantitation. By sorbing the solute onto the porous material and then, e.g., desorbing the solute with a substantially smaller volume of a less polar solvent, a solution which includes the solute of interest can be prepared having a substantially higher concentration of the solute of interest than that of the original solution. The method can also result in solvent exchange, that is, the solute is removed from a first solvent and re-dissolved in a second solvent.

Solvents which are suitable for desorbing the solute from the porous material can be, e.g., polar water-miscible organic solvents, such as alcohols, e.g., methanol, ethanol or isopropanol, acetonitrile, acetone, and tetrahydrofuran, or mixtures of water and these solvents. The desorbing solvent can also be, e.g., a nonpolar or moderately polar water-immiscible solvent such as dichloromethane, diethylether, chloroform, or ethylacetate. Mixtures of these solvents are also suitable. Preferred solvents or solvent mixtures must be determined for each individual case. A suitable solvent can be determined by one of ordinary skill in the art without undue experimentation, as is routinely done in chromatographic methods development (see, e.g., McDonald and Bouvier, eds., Solid Phase Extraction Applications Guide and Bibliography, "A Resource for Sample Preparation Methods Development," 6th edition, Waters, Milford, Mass. (1995); Snyder and Kirkland, Introduction to Modern Liquid Chromatography, New York: J. Wiley and Sons (1974)).

The level of the desorbed solvent present in the solvent can be analytically determined by a variety of techniques known to those skilled in the art, e.g., high performance liquid chromatography, gas chromatography, gas chromatography/mass spectrometry, or immunoassay.

The invention also provides separation devices comprising the porous materials of the invention. Such devices include chromatographic columns, cartridges, thin layer chromatographic plates, filtration membranes, sample clean up devices, solid phase organic synthesis supports, and microtiter plates. In certain embodiments, more than one type of functionalized porous material can be used in the separation devices, e.g., columns, cartridges, and the like.

As noted above, the porous materials of the invention are especially well suited for solid phase extraction. Thus, the invention also includes a solid phase extraction cartridge comprising a porous material of the invention packed inside an open-ended container. In one embodiment, the porous material is packed as particles within the open-ended container to form a solid phase extraction cartridge.

The container can be, e.g., a cylindrical container or column which is open at both ends so that the solution can enter the container through one end, contact the porous material within the container, and exit the container through the other end. In the form of porous particles, the porous material can be packed within the container as small particles, such as beads having a diameter between about 3 μm and about 500 μm, preferably between about 20 μm and about 200 μm. In certain embodiments, the porous particles can be packed in the container enmeshed in a porous membrane.

The container can be formed of any material which is compatible, within the time frame of the solid phase extraction process, with the solutions and solvents to be used in the procedure. Such materials include glass and various plastics, such as high density polyethylene and polypropylene. In one embodiment, the container is cylindrical through most of its length and has a narrow tip at one end. One example of such a container is a syringe barrel. The amount of porous material within the container is limited by the container volume and can range from about 0.001 g to about 50 kg, and preferably is between about 0.025 g and about 1 g. The amount of porous material suitable for a given extraction depends upon the amount of solute to be sorbed, the available surface area of the porous material and the strength of the interaction between the solute and the porous material. This amount can be readily determined by one of ordinary skill in the art. The cartridge can be a single use cartridge, which is used for the treatment of a single sample and then discarded, or it can be used to treat multiple samples.

EXAMPLES

The present invention may be further illustrated by the following non-limiting examples. All reagents were used as received unless otherwise noted. Those skilled in the art will recognize that equivalents of the following supplies and suppliers exist, and as such the suppliers listed below are not to be construed as limiting.

Example 1

To a 3000 mL flask was added a solution of 5.0 g hydroxypropylmethylcellulose (Methocel E15, Dow Chemical Co., Midland, Mich.) in 1000 mL water. To this was added a solution of 175 g divinylbenzene (DVB HP-80, Dow), 102 g N-vinylpyrrolidone (International Specialty Products, Wayne, N.J.), and 185 g azobisisobutyronitrile (VAZO 64, Dupont Chemical Co., Wilmington, Del.) in 242 g toluene (J. T. Baker, Phillipsburgh, N.J.). The 80% purity divinylbenzene above may be substituted with other hydrophobic monomers such as styrene or ethylvinylbenzene, or lower purity grades of divinylbenzene, but 80% purity divinylbenzene is preferred. The divinylbenzene is stripped with a sodium hydroxide solution prior to use in the normal way. The N-vinylpyrrolidone above may be substituted with other hydrophilic monomers such as N-vinylacetamide, N-vinylpyridine, methacrylate, methyl methacrylate, vinyl acetate, acrylamide, methacrylamide, but N-vinylpyrrolidone is most preferred.

The resulting biphasic mixture was stirred for 30 minutes at room temperature using sufficient agitation to form oil droplets of the desired micron size. The resulting suspension was then heated under moderate agitation at 70° C. and maintained at this temperature for 20 hours. The suspension was cooled to room temperature, filtered, and washed with methanol. The filter cake was then dried in vacuo for 16 hours at 80° C. The composition of the product polymer was determined by combustion analysis (CE-440 Elemental Analyzer; Exeter Analytical Inc., North Chelmsford, Mass., or equivalent). Elemental analysis N 2.24%; mole percent N-vinylpyrrolidone: 20%. A series of poly(divinylbenzene-co-N-vinylpyrrolidone) copolymers comprising about 13, 14, 16, and 22 mole % N-vinylpyrrolidone was also prepared by this method varying the starting ratio of the divinylbenzene and N-vinylpyrrolidone monomers.

Example 2

Poly(divinylbenzene-co-N-vinylpyrrolidone), OASIS® HLB, obtained from Waters Corp., Milford, Mass., was derivatized with hydrochloric acid (12 Molar, 36.5-38%, A.C.S. reagent, J. T. Baker, 9535-03, Phillipsburgh, N.J.) and paraformaldehyde (95%, Aldrich Chemical, 15, 812-7, Milwaukee, Wis.). A three-necked, round-bottom flask was fitted with a thermometer, agitator, condenser and reactor temperature control system. Hydrochloric acid was introduced into the flask. In some cases, water was added to the flask prior to hydrochloric acid addition in order to dilute the acid concentration to below 12 M. Then, the agitation and the temperature control were started. The agitator was a ground-glass shaft fitted through the proper Teflon bearing into the center opening atop the flask. The Teflon paddle was single-bladed. The agitation rate was adjusted to ensure adequate mixing. The poly(divinylbenzene-co-N-vinylpyrrolidone), OASIS® HLB, was charged. Next, the paraformaldehyde was charged. The reaction mixture was stirred for a certain period of time at constant temperature. The reaction mixture was cooled, and the acid solution was filtered. The chloromethylated poly (divinylbenzene-co-N-vinylpyrrolidone) copolymer was collected and washed with water until the pH of the slurry was $\geq 5.0$. In the case of Examples 2s and 2u, the copolymer was washed with water until the pH was $\geq 3$, and then a requisite amount of concentrated ammonium hydroxide was added to bring the pH between 8 and 9. The materials were then water washed until the pH was ~7. The filter cake of chloromethylated poly(divinylbenzene-co-N-vinylpyrrolidone) copolymer was then washed twice with methanol (HPLC grade, J. T. Baker, 9535-03, Phillipsburgh, N.J.) and dried in vacuo for 15 hours at 80° C. In the case of Examples 2t and 2u, the copolymer was dried directly from the water wet state with no methanol wash. The level of chloromethylation was determined by chlorine elemental analysis (Atlantic Microlab Inc., Norcross, Ga.). Reagent amounts, reaction conditions, and the resultant loading of chloromethyl groups ($CH_2Cl$) are listed in Table 1.

TABLE 1

| Product | Reaction Temperature (° C.) | Reaction Time (h) | HCl Molarity | Oasis ® HLB (g) | HCl (g) | Paraformaldehyde (g) | Chloromethyl Loading (meq/g) |
|---|---|---|---|---|---|---|---|
| 2a | 50 | 1 | 11.1 | 30 | 450 | 17 | 0.61 |
| 2b | 60 | 16 | 7.5 | 25 | 385 | 4.5 | 0.72 |
| 2c | 40 | 2 | 12.0 | 16 | 225 | 17 | 0.73 |
| 2d | 50 | 2 | 11.1 | 30 | 450 | 17 | 0.74 |
| 2e | 50 | 2 | 12.0 | 16 | 225 | 15 | 0.83 |

TABLE 1-continued

| Product | Reaction Temperature (° C.) | Reaction Time (h) | HCl Molarity | Oasis ® HLB (g) | HCl (g) | Paraformaldehyde (g) | Chloromethyl Loading (meq/g) |
|---|---|---|---|---|---|---|---|
| 2f | 50 | 6 | 11.1 | 30 | 450 | 17 | 0.89 |
| 2g | 50 | 16 | 11.1 | 30 | 450 | 17 | 1.00 |
| 2h | 60 | 16 | 9.0 | 25 | 385 | 14.5 | 1.01 |
| 2i | 70 | 2 | 11.1 | 30 | 450 | 17 | 1.03 |
| 2j | 60 | 5 | 12.0 | 16 | 250 | 8 | 1.14 |
| 2k | 60 | 16 | 10.5 | 25 | 385 | 14.5 | 1.15 |
| 2l | 70 | 16 | 1.1 | 30 | 450 | 17 | 1.23 |
| 2m | 70 | 6 | 11.1 | 30 | 450 | 17 | 1.24 |
| 2n | 60 | 25 | 12.0 | 16 | 250 | 8 | 1.35 |
| 2o | 65 | 21 | 12.0 | 5 | 150 | 8 | 1.38 |
| 2p | 70 | 25 | 12.0 | 61 | 926 | 51 | 1.43 |
| 2q | 65 | 24 | 12.0 | 500 | 9000 | 290 | 0.93 |
| 2r | 60 | 24 | 12.0 | 100 | 1500 | 58 | 1.09 |
| 2s | Same batch as 2r (10 g sample), but with ammonium hydroxide addition. | | | | | | 0.95 |
| 2t | 65 | 24 | 12.0 | 40 | 600 | 23.2 | 1.20 |
| 2u | Same batch as 2t (20 g sample) but with ammonium hydroxide addition | | | | | | 1.15 |

Example 3

Chloromethylated poly(divinylbenzene-co-N-vinylpyrrolidone) porous materials, prepared as described in Example 2, were reacted with the following amines (all purchased from Aldrich Chemical, Milwaukee, Wis.): Piperidine (PP), piperazine (PZ), N-methylpiperazine (MPZ), N-methylbenzylamine (MBZ) and morpholine (M). A general procedure is provided below. Reagent amounts, reaction conditions, and the resultant loading of amine groups are listed in Table 2.

A 250 mL, three-necked, round-bottom flask was fitted with a thermometer, agitator, condenser and reactor temperature control system. The amine was introduced into the flask, and the agitation and the temperature control were started. In the case of Examples 3b and 3g, the reaction suspension also included a charge of water. The agitator was a ground-glass shaft fitted through the proper Teflon bearing into the center opening atop the flask. The Teflon paddle was single-bladed. The chloromethylated poly(divinylbenzene-co-N-vinylpyrrolidone) was charged, and the agitation rate was adjusted to ensure adequate mixing. The reaction mixture was stirred for a certain period of time at constant temperature. The reaction mixture was cooled, and the amine was filtered. The aminated poly(divinylbenzene-co-N-vinylpyrrolidone) copolymer was collected and washed with water until the pH of the slurry was ≧7.0. The filter cake of aminated poly(divinylbenzene-co-N-vinylpyrrolidone) copolymer was then washed twice with methanol (HPLC grade, J. T. Baker, 9535-03, Phillipsburgh, N.J.) and dried in vacuo for 15 hours at 80° C. The loading of amine was determined by fully converting the amine to its hydrochloride salt with dilute hydrochloric acid, displace the chloride of the salt by exposing the material to dilute nitric acid, and then titrating the displaced chloride in solution with $AgNO_3$ (Metrohm 716 DMS Titrino autotitrator with silver electrode, Metrohm, Hersau, Switzerland, or equivalent).

TABLE 2

| Product | Temperature (° C.) | Reaction Time (h) | Chloromethyl product (g) | Chloromethyl load (meq/g) | Amine Type | Amine Amount (g or mL) | Amine Group Loading (meq/g) |
|---|---|---|---|---|---|---|---|
| 3a | 105 | 18 | 73 | 1.10 | PP | 730 g | 0.37 |
| 3b | 100 | 18 | 15 | 0.69 | PZ | 12.9 g in 150 mL water | 0.36 |
| 3c | 110 | 18 | 15 | 0.69 | MPZ | 150 | 0.43 |
| 3d | 110 | 18 | 15 | 0.69 | M | 150 | 0.16 |
| 3e | 110 | 18 | 20 | 1.24 | MBZ | 200 | 0.2 |
| 3f | 110 | 18 | 20 | 0.93 | M | 135 | 0.18 |
| 3g | 100 | 18 | 20 | 0.93 | M | 17.5 mL in 100 mL water | 0.17 |

Example 4

This example illustrates the preparation of poly(divinylbenzene-co-N-vinylpyrrolidone) and poly(divinylbenzene-co-N-vinylpyrrolidone-co-vinylbenzylchloride) monolithic copolymers. A general procedure is provided below. Reagent amounts, reaction conditions, and characterization data are listed in Table 3.

To a 20 mL glass vial was added N-vinylpyrrolidone (NVP, Aldrich Chemical, Milwaukee, Wis.), divinylbenzene (DVB HP-80, Dow), cyclohexanol (CH, Aldrich Chemical, Milwaukee, Wis.), dodecanol (DD, Aldrich Chemical, Milwaukee, Wis.) and azobisisobutyronitrile (VAZO 64, Dupont Chemical Co., Wilmington, Del.). In some cases Vinylbenzyl chloride was also added (VBC, Fluka, Milwaukee, Wis.). These mixtures were mixed and purged with nitrogen for 5 minutes before 5 mL aliquots were transferred to individual 10 mL glass vials. Each of these vials was placed in an oven at 75° C. for 24 hours. Following removal from the vials, each monolith was placed in refluxing methanol for 32 hours and then dried for 24 hours at 75° C. and an additional 24 hours at 85° C. under vacuum. The level of chloromethylation was determined by chlorine elemental analysis (Atlantic Microlab Inc., Norcross, Ga.). Reagent amounts, % C, porosity data, and the resultant loading of chloromethyl groups ($CH_2Cl$) are listed in Table 3.

The % C was determined as in Example 1. The resultant loading of chloromethyl groups ($CH_2Cl$) was determined as in Example 2. The specific surface areas (SSA), specific pore volumes (SPV) and the average pore diameters (APD) of these materials were measured using the multi-point $N_2$ sorption method (Micromeritics ASAP 2400; Micromeritics Instruments Inc., Norcross, Ga., or equivalent). The specific surface area was calculated using the BET method, the specific pore volume was the single point value determined for $P/P_0 > 0.98$, and the average pore diameter was calculated from the desorption leg of the isotherm using the BJH method. The macropore pore volume (MPV) of the resultant materials was measured by Mercury Porosimetry (Micromeritics AutoPore II 9220 or AutoPore IV Micromeritics, Norcross, Ga., or equivalent).

TABLE 3

| Product | NVP (g) | DVB (g) | CH (g) | DD (g) | AIBN (g) | VBC (g) | % C | SSA ($m^2/g$) | TPV ($cm^3/g$) | APD (Å) | Cl (meq/g) | MPV (mL/g) |
|---|---|---|---|---|---|---|---|---|---|---|---|---|
| 4a | 2.2 | 3.9 | 10.8 | 1.2 | 0.08 | 0 | 81.9 | 394 | 0.72 | 120 | 0 | 0.54 |
| 4b | 2.2 | 3.3 | 10.8 | 1.2 | 0.08 | 0.76 | 87.3 | 657 | 1.31 | 117 | 0.92 | 1.42 |
| 4c | 2.0 | 3.5 | 10.8 | 1.2 | 0.08 | 0.76 | 87.1 | 653 | 1.25 | 112 | 0.89 | 1.48 |

Example 5

Monoliths of the type 4b were placed in 100 mL round bottom flasks equipped with reflux condensers, containing 50 mL of either methylpiperazine (MPZ), N-methylbenzylamine (MBZ) (Aldrich Chemical, Milwaukee, Wis.). The flasks were heated for 16 hours, at which point, they were cooled and the monoliths removed. The monoliths were then placed in refluxing methanol for 24 hours (replaced with fresh methanol after 12 hours), before being dried for 24 hours at 85° C. under vacuum. Amine type, reaction temperature, and the resultant loading of amine groups are listed in Table 4. The % C and % N were determined as in Example 1. The loading of amine was determined as described in Example 3.

TABLE 4

| Product | Amine | Temperature (° C.) | % C | % N | Amine Load (meq/g) |
|---|---|---|---|---|---|
| 5a | MPZ | 110 | 86.6 | 2.75 | 0.36 |
| 5b | MBZ | 140 | 89.5 | 1.74 | 0.14 |

Example 6

Figure 2:
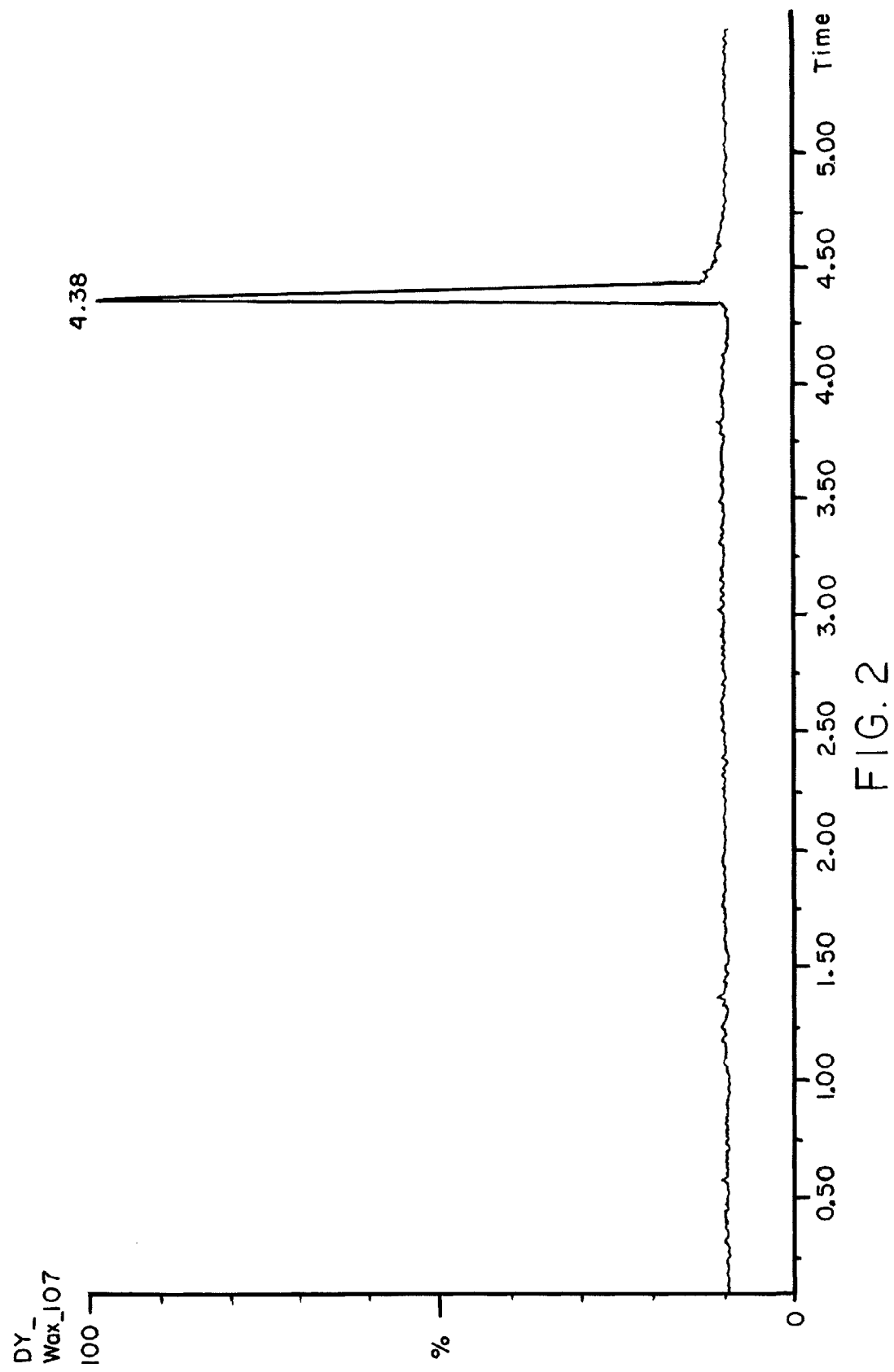
FIG. 2 depicts the total ion chromatogram (TIC) obtained using the product of Example 3f.

Products of Example 3b and 3f were placed in 2.1×20 mm chromatographic columns were using a slurry packing technique. The packed columns were subsequently employed in an modular valve switching system comprising a 2777 Sample Manager, a 1525μ Binary HPLC pump, a 2-Position, 6-Port Solvent Selector Valve (two total), a 515 HPLC pump, (two total), a Quattro Ultima Pt detector, and MassLynx 4.0 software (all from Waters Corporation, Milford, Mass., or equivalent). An 80 μL injection of dipyrone (Sigma-Aldrich, Milwaukee, Wis.) in a water solution (10 ng/mL) was loaded onto the column in a water mobile phase containing 3% formic acid for 1 minute at 4 mL/min. The column was then washed with a methanol solution containing 3% formic acid for 1 minute at 4 mL/min. The dipyrone was then eluted from the column with a 95:5 (v/v) methanol:3% $NH_4OH$ water mobile phase at 0.4 mL/min. FIGS. 1 and 2 show the total ion chromatograms (TIC) for the elution of dipyrone using the products of Example 3b and 3f respectively.

Example 7

Products of Example 3b and 3f were placed into 1 cc cartridges (30 mg/cartridge) using a dry packing technique. Each cartridge was conditioned with 1000 μL methanol and then conditioned with 1000 μL water. A 1000 μL sample was loaded which consisted of isotonic saline spiked with the following analytes: 2-naphthalenesulfonic acid (2.5 μg), amitriptyline (5 μg), ketoprofen (15 μg), salicylic acid (7.5 μg), secobarbital (12.5), 4-propylbenzoic acid (15 μg). Each loaded cartridge was washed with 1000 μL 25 mM sodium acetate, pH=4 (designated Fraction 1), and then washed with 1000 μL of methanol (designated Fraction 2). Next each cartridge was eluted with 1000 μL of 2% ammonium hydroxide in 20:80 (v:v) methanol-acetonitrile (designated Fraction 3) and then eluted again with 500 μL of 2% ammonium hydroxide in 20:80 (v:v) methanol-acetonitrile (designated Fraction 4). All fractions after the equilibration were collected, and 500 μL of 0.1 mg/mL butyl paraben in acetonitrile was added as an internal standard. Fraction 1 was then diluted with 1000 μL of 2% formic acid in 20:80 (v:v) methanol-acetonitrile. Fractions 2 and 3 were then diluted with 1000 μL of saline. Fraction 4 was diluted with 500 μL of saline. All fractions were diluted with 100 μL of concentrated phosphoric acid prior to injection. All analytes were from Sigma-Aldrich (Milwaukee, Wis.), all reagents were from J. T. Baker (Phillipsburgh, N.J.).

Each fraction was measured for sample recovery using the following HPLC equipment and method (all from Waters Corporation, Milford, Mass. or equivalent): Waters 600 HPLC pump; Waters 717 autosampler; Waters 486 UV detector; 3.5 μm SymmetryShield™ $RP_8$ column, 4.6×75 mm; Mobile phase 68:32 (v:v) 20 mM $K_2HPO_4$, pH 2.7—acetonitrile; Flow rate was 2.0 mL/min; Temperature 35° C. Detection UV at 214 nm. Injection volume 15 μL. Percent recoveries and the corresponding % RSD are listed in Table 5 for the average of two runs.

TABLE 5

| | Analyte | | | | |
| | % Analyte Recovery | | | | |
| Product | Fraction 1 | Fraction 2 | Fraction 3 | Fraction 4 | % RSD |
|---|---|---|---|---|---|
| 3b | | | | | |
| 2-naphthalenesulfonic acid | 0.0 | 0.0 | 97.6 | 0.0 | 0.05 |
| amitriptyline | 0.0 | 93.3 | 0.0 | 0.0 | 0.53 |
| ketoprofen | 0.0 | 0.0 | 96.3 | 0.0 | 0.18 |
| salicylic acid | 0.0 | 0.0 | 96.7 | 0.0 | 0.25 |

TABLE 5-continued

| | Analyte | | | | |
|---|---|---|---|---|---|
| | % Analyte Recovery | | | | |
| Product | Fraction 1 | Fraction 2 | Fraction 3 | Fraction 4 | % RSD |
| secobarbital | 0.0 | 94.0 | 0.0 | 0.0 | 0.08 |
| propylbenzoic acid 3f | 0.0 | 0.0 | 95.2 | 0.0 | 0.01 |
| 2-naphthalenesulfonic acid | 0.0 | 0.0 | 92.5 | 1.1 | 2.33 |
| amitriptyline | 0.0 | 93.5 | 0.0 | 0.0 | 1.86 |
| ketoprofen | 0.0 | 91.8 | 2.8 | 0.0 | 1.45 |
| salicylic acid | 0.0 | 4.3 | 88.4 | 0.0 | 0.97 |
| secobarbital | 0.0 | 94.7 | 0.0 | 0.0 | 1.27 |
| propylbenzoic acid | 0.0 | 96.7 | 0.0 | 0.0 | 1.04 |

INCORPORATION BY REFERENCE

The entire contents of all patents, published patent applications and other references cited herein are hereby expressly incorporated herein in their entireties by reference.

EQUIVALENTS

Those skilled in the art will recognize, or be able to ascertain using no more than routine experimentation, numerous equivalents to the specific procedures described herein. Such equivalents were considered to be within the scope of this invention and are covered by the following claims. The contents of all references, issued patents, and published patent applications cited throughout this application are hereby incorporated by reference.

What is claimed is:

1. A method for removing or isolating a component from a mixture comprising:
    contacting the mixture with a chromatographic material comprising a porous material comprising a copolymer of at least one hydrophobic monomer and at least one hydrophilic monomer, wherein said copolymer further comprises at least one ion-exchange functional moiety comprising a piperazinyl moiety, to thereby remove or isolate the component from the mixture;
    wherein said hydrophilic monomer is N-vinylpyrrolidone.

2. A method for determining the level of a component in a mixture, comprising:
    contacting the mixture with a chromatographic material comprising a porous material comprising a copolymer of at least one hydrophobic monomer and at least one hydrophilic monomer, wherein said copolymer further comprises at least one ion-exchange functional moiety comprising a piperazinyl moiety under conditions that allow for sorption of the component onto the porous material;
    washing the chromatographic material having the sorbed component with a solvent under conditions so as to desorb the component from the porous materials; and
    determining the level of the desorbed component;
    wherein said hydrophilic monomer is N-vinylpyrrolidone.

* * * * *